United States Patent
Sherman et al.

(10) Patent No.: US 8,323,899 B2
(45) Date of Patent: Dec. 4, 2012

(54) SILICA MAGNETIC PARTICLES WITH A HIGH NUCLEIC ACID BINDING CAPACITY

(75) Inventors: David Sherman, Davis, CA (US);
Karlheinz Hildenbrand, Krefeld (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 492 days.

(21) Appl. No.: 12/524,819

(22) PCT Filed: Feb. 1, 2008

(86) PCT No.: PCT/US2008/052761
§ 371 (c)(1),
(2), (4) Date: Jul. 28, 2009

(87) PCT Pub. No.: WO2008/095155
PCT Pub. Date: Aug. 7, 2008

(65) Prior Publication Data
US 2010/0009375 A1    Jan. 14, 2010

Related U.S. Application Data

(60) Provisional application No. 60/887,633, filed on Feb. 1, 2007.

(51) Int. Cl.
*C12Q 1/68* (2006.01)
(52) U.S. Cl. ........................ 435/6.12; 435/6.1
(58) Field of Classification Search ................ 435/91.2, 435/6.12
See application file for complete search history.

(56) References Cited

U.S. PATENT DOCUMENTS

| 4,280,918 A | 7/1981 | Homola et al. |
| 7,223,331 B2 * | 5/2007 | Stark et al. ............... 208/108 |
| 2010/0063263 A1 * | 3/2010 | Hennig et al. ............ 536/23.1 |

FOREIGN PATENT DOCUMENTS

| WO | 03058649 | 7/2003 |
| WO | 2004003231 | 1/2004 |
| WO | 2006136314 | 12/2006 |

OTHER PUBLICATIONS

Aliev et al., Adv. Mater., vol. 11, No. 12, pp. 1006-1010, 1999.*
Sun et al., Journal of Magnetism and Magnetic Materials, vol. 285, pp. 65-70, 2005.*
International Search Report dated Sep. 16, 2008 for WO 2008/095155.
EP Search Report for App. No. 08714166.9 dated Oct. 12, 2011.

\* cited by examiner

*Primary Examiner* — Gary Benzion
*Assistant Examiner* — Cynthia Wilder

(57) ABSTRACT

Magnetic particles for nucleic acid isolation are coated with silica and separated from impurities and nanoparticulates using a multi-step fractionation process. In each cycle of the fractionation process, the particles are stirred, sedimented, and resuspended, resulting in a decline in pH of the suspended particles. Repeating the fractionation process until the resuspended particles have dropped to a target pH in the range of about 9 to 10.5, and their zeta potential is more negative than about −40 mV, results in a purified population of particles with a high and reproducible binding capacity for nucleic acids. The silica-treated magnetic beads produced by the method offer improved sensitivity and consistency for recovery of nucleic acids in a sample.

34 Claims, No Drawings

SILICA MAGNETIC PARTICLES WITH A HIGH NUCLEIC ACID BINDING CAPACITY

CROSS REFERENCE TO RELATED APPLICATIONS

The present application claims priority to U.S. Application No. 60/887,633, filed on Feb. 1, 2007, the entire contents of which are incorporated herein by reference.

BACKGROUND OF THE INVENTION

The magnetic particle process is increasingly being used as a high-throughput process for the automatic isolation of nucleic acids, in which total nucleic acid (both DNA and RNA) is isolated from a biological sample matrix by reversible binding to SiOH-modified magnetic particles. For this purpose the nucleic acids to be isolated are contacted with silica-modified magnetic particles in a chaotropic binding buffer. The binding of the nucleic acids to the particle surface takes place over a range of temperatures, from ~18° to ~38° C. for example, over a period of time up to an hour while the particle suspension is mixed by shaking or vortexing. The particles loaded with nucleic acids are then drawn towards the vessel wall by applying a magnetic field, and the supernatant is aspirated and discarded. After removing the magnetic field, the particles are resuspended and washed several times with a washing buffer or buffers. The nucleic acids bound to the magnetic particles are then removed from the particles at a high temperature, such as for example at 90° C. for 10 mins, with the aid of an elution buffer. After re-applying the magnetic field, the eluate containing the nucleic acids can be pipetted off. This process is described in detail in WO 2003/058649.

Ideally, magnetic particles for the automated isolation of nucleic acids (NA) are distinguished by a balanced combination of specific requirements with regard to particle size, silica content on the particle surface, magnetic properties, and purity. Magnetic particles of $Fe_3O_4$ (magnetite), such as for example the Bayoxide E types from Lanxess, which are used as electrographic toners, are commercially available magnetic particles that fulfill these properties to a certain degree.

The primary particle sizes of the Bayoxide E magnetic particles as determined by electron microscopy are in the range from about 0.2 to about 0.4 µm. This corresponds to a (BET) specific surface area in the range of a few $m^2/g$, i.e. of about 4 to 12 $m^2/g$, with the particularly preferred Bayoxide E 8706 particles having a specific surface area of 7 to 9 $m^2/g$. Useful suspension stabilities can be obtained with magnetic particles having such particle size distributions.

On the one hand, in order to obtain the maximum possible quantitative binding of nucleic acids, the suspension stability should be such that the suspension of particles obtained by shaking in the binding buffer is as homogeneous as possible. On the other hand, the magnetic particles loaded with nucleic acids have to be completely removed within a short time after applying the magnetic field, such as within one minute, in order to obtain the shortest possible analysis time for high throughput methods.

Although magnetic particles with smaller diameters (e.g., "magnetic nanoparticles" or "nanoparticulate Bayoxides") form highly stable suspensions, they require considerably longer times for their removal by the magnetic field. Magnetic particles with larger particle sizes (e.g., several µm) form suspensions whose stability is too low, which can have a negative effect on the adsorption of the nucleic acids.

Although the abovementioned Bayoxide E magnetic particles (e.g., Bayoxide E 8706 and Bayoxide E 8707) are suitable for nucleic acid analysis, these products also contain small quantities of nanoparticulate components which manifest themselves in the form of black dust. These nanoparticulates can bind considerable quantities of DNA due to their large surface area, yet they can only be removed with great difficulty by the magnetic field. Considerable losses in yield are therefore likely to occur in the nucleic acid isolation process as a result of these nanoparticulate components.

Commercially obtainable Bayoxide E magnetic particles also have been found to contain an additional form of nanoparticulate impurity, namely yellow-colored boehmite crystals (α-FeOOH). Boehmite crystals can be obtained in varying quantities depending on the production batch, and are formed due to a side reaction during the synthesis of magnetite (i.e., by the oxidation of $FeSO_4$ at alkaline pH values). These particles are not magnetic but can bind nucleic acids, particularly when they are treated with silica, and therefore prevent a certain fraction of the nucleic acids in a sample from being removed magnetically.

Residues of the starting product, iron sulfate, have also been found in Bayoxide E magnetic particles as a third type of impurity. Although these iron salts cannot bind nucleic acids they are nevertheless disadvantageous since they can poison the enzymes used in PCR, which is frequently used for subsequent detection. Also, iron ions can form colored secondary products with the chaotropic buffer systems frequently used for nucleic acid isolation, which may contain guanidinium isothiocyanate, for example. These secondary products can considerably interfere with photometric analysis used in nucleic acid detection processes.

Aqueous suspensions of the abovementioned Bayoxide E particles are also disadvantageous because they have a relatively high affinity for vessel walls of glass or plastic, and considerable quantities of the magnetic particles can be adsorbed to such walls. More advantageous particle suspensions are those which flow off vessel walls leaving as little residue as possible, especially from microtiter plates made of thermoplastics, which are frequently used for nucleic acid isolation.

Industrially produced magnetic particles also exist which, as a result of the method employed for their production, contain small quantities of silica and display a certain nucleic acid binding capacity. In the synthesis of Bayoxide E 8706 and Bayoxide E 8707, for example, waterglass (an alkali metal silicate solution) is added in order to render the particles more spherical and less sharp-edged. The silica concentration available on the surface, and thus the nucleic-acid-binding capacity, of these particles is low, however, and also varies from batch to batch. Due to the resulting reduced nucleic acid binding capacities, relatively large quantities of such magnetic particles would have to be used for nucleic acid isolation, making it difficult or impossible to effectively process smaller volumes of nucleic acid samples.

Thus, there remains a need for magnetic particles with appropriate nucleic acid binding properties, magnetic separation properties, and freedom from chemical contaminants in order to improve yield, consistency, and throughput during nucleic acid isolation and analysis.

BRIEF SUMMARY OF THE INVENTION

The invention provides a process of preparing silica-coated magnetic particles. Such particles are particularly well suited for the binding and recovery of nucleic acids from a sample for subsequent analysis, such as in the high throughput identification of an organism present in the sample. Particles made by the process of the invention have superior properties for nucleic acid binding because the particles have been purified away from reaction by-products and nanoparticulates originally present in the original magnetic particles, which otherwise might interfere with nucleic acid recovery or detection.

In one aspect, the invention provides a process of fractionating silica-coated magnetic particles. The process includes the steps of reacting magnetic particles with waterglass, sedimenting the particles, resuspending the sedimented particles to form an aqueous suspension, and repeating the sedimentation and resuspension steps until the pH of the aqueous suspension is in the range from about pH 9.4 to about pH 10.0. In a preferred embodiment, the pH is in the range of 9.7+/−0.2. In another preferred embodiment, the zeta potential of the particles at pH 7 is more negative than −40 mv. In yet another embodiment, the zeta potential is in the range of about −48 to about −58 mV at pH 7.

Another aspect of the invention is a method of analyzing a nucleic acid in a sample. The method includes binding the nucleic acid in the sample to a suspension of silica-coated magnetic beads produced according to the process described above.

Yet another aspect of the invention is a kit including a population of silica-coated magnetic particles made by the process described above. The kit further includes instructions for the use of the particles in a method of isolating or analyzing a nucleic acid.

DETAILED DESCRIPTION OF THE INVENTION

The present invention relates to a new process for the modification with silica of spherical magnetic particles used for the automated isolation of nucleic acids in high throughput processes. Silica is deposited on the particle surface from an alkaline waterglass solution by reducing the pH value without the addition of an acid. This process is characterized by reducing the pH through the addition of water in a multi-step fractionation process. The target product is purified after each individual step, for example, by sedimentation. The multi-step fractionation process can be repeated a number of times until a pH value preferably in the range of about 9.5 to about 9.9 is obtained in the aqueous magnetic particle suspension.

The silica-modified magnetic particles thus obtained are characterized in that the magnetic properties of the original magnetic particles remain virtually unchanged and their modification with silica does not produce any significant broadening of the particle size distribution. On the contrary, the multi-step fractionation process leads to the separation of so-called nanoparticulate impurities and iron salts of the kind typically contained in commercially available magnetic particles.

Using the silica-modified magnetic particles produced according to the invention, consistent recovery rates can be obtained in the automated isolation of nucleic acids over a 6-7 log range of nucleic acid concentration.

Magnetic Particles

Magnetic particles for use in the invention can contain a ferromagnetic material such as magnetite ($Fe_3O_4$) that renders them magnetic. Furthermore, magnetic particles for use in the invention have diameters in the μm range, such as having an average particle diameter of about 0.5 to about 1.5 μm, or about 0.1 to about 1 μm. Their small size renders them stable for several minutes in aqueous suspension and gives them a high binding capacity for nucleic acids when coated with a thin layer of silica. Their size is sufficiently large to be capable of sedimentation in a magnetic field within minutes, e.g., for harvesting bound nucleic acids. Suitable magnetic particles include, for example, materials sold by Lanxess under the name Bayoxide E.

The abovementioned Bayoxide E magnetic particle types possess magnetic properties that make them ideally suited for nucleic acid isolation. For example, the preferred Bayoxide E 8706 type has Bs (saturation) values in the range of 84.8-93.5 emu/g, whereas the Br (remanence) values are merely 4.7-7.3 emu/g. Their iHc coercivity is in the range of 45-65 Oe. Accordingly, these magnetic particles can be removed quickly and effectively at relatively low magnetic field strengths, and their magnetic properties subside very quickly after removing the magnetic field, thus facilitating resuspension.

Additional literature on the subject of "magnetism" can be found in the 10th edition of "Rbmpp Lexikon Chemie" (Rbmpp's Chemical Encyclopedia).

The following is a summary of the properties of Bayoxide E 8706, a preferred type of magnetic particles for use in the invention, and the type used in the working examples described below. Manufacturer: Lanxess AG, Leverkusen; Use: Electrographic toners Magnetic properties: Remanence Br: 4.7-7.3 emu/g, saturation magnetism Bs: 84.8-93.5 emu/g, coercivity: iHc: 45-65 Oe. The magnetic data were determined according to AFAM 2350-1250101-02D. BET: 7-9 $m^2$/g determined according to DIN 66 131. pH: 5.5-8.0 determined according to DIN EN ISO 787/9. Iron oxide content: >95% determined as $Fe_2O_3$ according to AFMA 2301-0270502-02D. Density: 4.6 g/ml according to DIN EN ISO 787. Predominant particle size: 0.3 μm determined using an electron microscope.

In the examples presented below, the magnetic flux density B (emu/g) was determined as a function of the magnetic field strength H, the analytical characteristic obtained being the so-called hysteresis curve, as explained for example in "Rbmmp Chemielexikon". The most important analytical values are as follows: saturation magnetism (Bs(emu/g)); remanence flux density (Br(emu/g)), which is the remaining magnetism after the removal of the externally applied magnetic field); and iHc (Oe), which is the coercive force necessary to reduce the remanence flux density to zero. The measurements were carried out in an induction magnetometer with a measured field strength of 5 kOe.

Silica Coating and Fractionation Process

The abovementioned Bayoxide E magnetic particles, and in particular the readily available Bayoxide E 8706 type, can be coated with silica in such a manner as to retain their excellent magnetic properties and particle size distribution while at the same time maximizing their nucleic acid binding capacity. In order to maintain the magnetic properties and particle size distribution of the particles, the silica content should remain as low as possible. However, in order to achieve a high nucleic acid binding capacity, a high SiOH density on the magnetic particle surfaces is advantageous. In addition, the required silica-modified magnetic particles must be as free as possible from the abovementioned nanoparticulate impurities and chemical impurities such as iron ions. The particles according to the invention preferably should also have advantageous run-off properties, especially from plastic vessels containing materials such as polyethylene, polypropylene, or polystyrene. The method of the present invention also should produce substantially identical silica-modification of magnetic particles independently of the surface pH value of the particles. This aspect is important since surface pH value of magnetic particles can vary considerably. For example, the Bayoxide E 8706 particles are produced with a surface pH value, determined according to DIN EN ISO 787/9, varying over the range from 5.0 to 7.5.

WO 2003/058649 describes an elegant prior art process for the deposition of silica on Bayoxide E magnetic particles from Lanxess using waterglass solutions, such as waterglass HK 30 from Cognis. The process described in WO 2003/058649 is remarkably simple. The magnetic particles employed are Bayoxides with slightly acidic pH values, such as Bayoxide E 7807, which is specified as having a pH value of 6.5. It is postulated that the acidic Bayoxide E 8706 particle surface induces waterglass/silica precipitation. The magnetic particles are suspended in a dilute waterglass solution and stirred for 30 minutes. After filtration, the filter cake is washed five times with water and once with ethanol and then dried for five hours at 80° C. in order to stabilize the silica coating. Whereas this process is remarkable for its simplicity, the end product is not optimal, since a lumpy product is obtained which has to be repulverized by mortaring or grinding. The particle size distribution of these products is dependent on the mortaring or grinding process. Frequently, macroparticles are obtained as a result of aggregation. Their particle size distributions can be four to ten times broader than the more suitable particle size distribution of Bayoxide E. Beside the coarsely divided aggregates, which have unfavorable suspension stability, nanoparticulate impurities are also contained in these products. These nanoparticulate impurities (black nanoparticulate Bayoxides and yellow nanoboehmites) cannot be removed in conventional filtration processes even by intense washing, since extremely dense filtration layers are produced by filter cake formation. If the silica-modified magnetic particles described in WO 2003/058649 are resuspended in water or buffer solutions, more or less cloudy or colored aqueous supernatants are frequently obtained on leaving such suspensions to stand, depending on the batch. The degree of this cloudiness or coloring depends on the content of the above-mentioned nanoparticulate impurities or iron salt impurities.

Wo 2006/136314, which is based on similar raw materials, describes an alternative process in which the deposition of silica from waterglass, through the continuous lowering of the pH value, is carried out by cross-flow microfiltration. Permeation with water is carried out until the permeate has reached an almost neutral pH value (7.0 to 7.5). This continuous filtration method, which requires more than 12 hours, is intended to remove nanoparticulates and colored secondary products. However, the continuous membrane process described in WO 2006/136314 cannot produce the required purification effects under production conditions. Although the nanoparticulate impurities can generally be filtered off via membranes with a pore size of 0.1 or 0.2 μm, very dense secondary filter layers are formed under practical conditions within a relatively short period due to the partial blockage of the membrane pores, even under cross-flow conditions. Under these conditions the nanoparticulate impurities are also retained. In addition, as described in the examples below, the nucleic acid binding capacity of the silica-modified magnetic particles produced by a continuous membrane process is also greatly reduced. In this process particles are obtained which at best have a zeta potential of −41 mV, which points to a relatively low concentration of SiOH groups on the particle surface. It has been found that zeta potential values of about −50 mV, or more negative values, are preferred in order to obtain high nucleic acid binding capacities.

The inventors have surprisingly found that the desired properties of magnetic particles for nucleic acid recovery and analysis (e.g., Bayoxide E particles with an optimum surface SiOH content but without any disadvantageous nanoparticulate components) can be obtained by a multi-step fractionation process. Without intending to limit the invention in any way, it appears that the washing and sedimentation process described herein leads to the separation of undesired contaminants and at the same time produces a gradual lowering of the pH such that a thin silica layer is polymerized on the surface of the magnetic particles, producing particles with essentially unaltered magnetic properties and a high degree of nucleic acid binding.

This process begins with the stirring of magnetic Bayoxide E particles in a dilute waterglass solution (the reaction step). The magnetic particles are suspended in a waterglass solution at a particle concentration of about 0.2 to about 0.4% (w/v). The concentration of waterglass can be in the range from about 0.2 to about 10% (w/v), and is preferably about 6.25% (w/v). The suspension is stirred in order to keep the particles suspended during the reaction. For example, an anchor stirrer can be used at a speed of about 200 to about 300 rpm. The reaction is carried out at room temperature, or in the range of about 15° C. to about 40° C. The alkaline pH of the reaction mixture can be set by the waterglass solution, and is generally about pH 10 to about pH 13. Preferably the pH of the reaction mixture is 12 to 13. The reaction mixture preferably contains only magnetic particles and a solution of waterglass in deionized water. No added buffers, salts, or other components are required; although other components can be added, care should be exercised to prevent alteration of either the polymerization rate or form of silica on the particles or the removal of contaminants by sedimentation.

While the reaction step is similar to the reaction step described in WO 2003/058649, unlike in that reference the reaction mixture is not filtered off and dried. Instead, the reaction mixture is left to stand, e.g., for about one hour at 1×g (i.e., under normal gravity, without applying any stirring, magnetic field, or centrifugal force), at about 15° C. to about 40° C. (the sedimentation step). Optionally, sedimentation can be accelerated by applying a magnetic field or centrifugal force to direct the silica coated magnetic particles towards a wall of the vessel; however, co-sedimentation of contaminating nanoparticles should be avoided when adjusting the sedimentation conditions. During the sedimentation step, the magnetic particles partially modified with silica are preferentially sedimented, whereas the nanoparticulate secondary products (magnetic nanoparticles and colored boehmite nanoparticles) and the incompletely reacted iron sulfate remain in the supernatant.

The supernatant, containing the impurities, is siphoned off with the aid of a glass tube down to just above the level of the sedimented particles and discarded. Typically, the boundary between the supernatant and the sedimented particles is not sharp; therefore, a balance should be struck between leaving too much supernatant (and therefore residual contamination) and removing too much supernatant (and therefore incurring loss of particles). Preferably, the removal of the supernatant is performed so that not more than 10% of the silica coated particle product is lost after each sedimentation step. Deionized water is added to the residue, and the mixture is stirred again. As above, no added buffers, salts, or other components are required, but can be added if care is taken to avoid co-sedimentation of undesired nanoparticulates. Stirring parameters can be the same as or similar to stirring during the reaction step (e.g., 30 min at 200-300 rpm, carried out at about 15° C. to about 40° C.). After the period of stirring, the particles are again left to sediment for about one hour at 1×g and about 15° C. to about 40° C., after switching off the stirrer. Again, sedimentation time can be reduced by applying a magnetic field or centrifugal force while avoiding co-sedimentation of contaminants.

A "multi-step fractionation process" according to the invention includes the initial reaction step followed by one or more "working cycles", each cycle including sedimentation of the magnetic particles, removal of the supernatant, and resuspension of the particles in water or an aqueous solution. The original pH value of the initial reaction mixture naturally falls as a result of the addition of water during resuspension of the particles. The pH is reduced by about 0.5 to 0.1 pH units per working cycle.

Any one or more of the particle sedimentation steps can be generally accelerated by applying either a magnetic field or a centrifugal field, or both. However, it may be advantageous to adhere to a specific period of time, such as an hour, for each sedimentation step. The reaction time can set at 30 minutes at room temperature, for example. By raising the temperature the reaction rate may possibly be increased and the reaction time shortened accordingly. In order to prevent particle aggregation, the end product preferably is not dried, but is processed in the form of an aqueous suspension. If the particle suspension is dried, then some particle aggregation may occur, which can be reversed by sonication of the resuspended particles. Even if the particle suspension is not dried, sonication can be used to reduce the likelihood of aggregates in the particle suspension. For example, a sonicator wand or bath can be used for a period from about 1 to about 5 minutes to disrupt aggregates that might be present in a particle suspension, particularly after storage.

An important aspect of a multi-step particle fractionation process of the invention is to stop the rinsing procedure at an appropriate endpoint. The inventors have unexpectedly found that the good nucleic acid binding capacity is obtained by repeating the fractionation process until a target pH value in the range of 9.0 to 10.5 is obtained. Preferably, the target pH is in the range of 9.4 to 10.0, or 9.5 to 9.9, or 9.4 to 9.8, which results in better nucleic acid binding capacity. In general, the final particle suspension should have a zeta potential that is at least −40 mV, or more negative than −40 mV, when measured at pH 7. In a more preferred embodiment, the target pH is about 9.7. When this pH range is achieved, the corresponding particles should have a zeta potential in the range of −48 to −58 mV, as measured at a pH of 7. If, on the other hand, the multi-step fractionation process is continued until, for example, a pH value of 7.0 to 7.5 is obtained, the nucleic acid binding efficiency will be considerably reduced, and the zeta potential is reduced to the range from −41 to −35 mV, as measured at a pH of 7 (see examples for further details). According to a non-limiting theory of the invention, the pH of the final particle suspension determines the density of $SiO^-$ groups on the silica coating, which in turn sets the zeta potential. Either pH or zeta potential, or both, can be used to define the endpoint of the wash procedure.

The nucleic binding capacity of the final product is such that a target nucleic acid can be bound and subsequently detected, for example by quantitative PCR, when present as low as 100 copies per mL of sample. More preferably, the final product can be used to isolate and detect a target nucleic acid as low as 50 copies/mL; most preferably it can bind and be used to detect down to 20 copies/mL.

In a preferred embodiment, the pH value of the final aqueous magnetic particle suspension is stabilized with the aid of a buffer. An example of a suitable buffer for the target pH range of 9.5 to 9.8 is 2-cyclohexylaminoethane-sulphonic acid (CHES). In order to obtain particles in the desired target ranges of pH and zeta potential, anywhere from 5 to 15 working cycles may be required. Using this procedure a total preparation time of about 12 hours is generally required.

The following is a description of Sodium Silicate 37/40, a preferred sodium silicate for use in the invention and the material used in the working examples. Manufacturer: Cognis Deutschland GmbH, Düsseldorf. Density: 1345-1355 kg/m$^3$ determined by the vibration process. Viscosity: 50-100 mPas determined using a Höppler viscosimeter. $Na_2O$ content: 7.80-8.20%, determined using a potentiometer. $SiO_2$ content: 26.6-27.0, determined using a potentiometer. Calculated $SiO_2/Na_2O$ weight ratio: 3.30-3.51. Calculated $SiO_2/Na_2O$ molar ratio: 3.41-3.51.

Particle Size Distribution

The primary magnetic particles used in the reaction step should be essentially monodisperse and free from aggregates. Also, after silica coating and fractionation, it is preferred that the particles be essentially monodisperse for optimal nucleic acid binding properties. Therefore, the particle size distribution can be analyzed both before and after a multi-step fractionation procedure according to the invention. Bayoxide E 8706 particles have an average diameter of 0.2-0.4 µm as determined by scanning electron microscopy (SEM). However, it is not possible to determine by the SEM method whether the particles are in a monodisperse or agglomerated form.

Methods that can be used to determine the particle size distribution include dynamic laser light scattering method (DLS) and analytical ultracentrifugation (AUC). Different values may be obtained for identical particle systems depending on which method of analysis is used; see, e.g., "Particle Characterization", Part. Part. Syst. Charact., 12 (1995) 148-157. Analytical ultracentrifugation uses a separation principle based on differing sedimentation rates as a function of particle size, and is preferred because it usually allows the determination of bi- or trimodal distributions in addition to monomodal distributions. Conventional laser light scattering methods usually do not allow the analysis of bi- or trimodal distributions. The pretreatment of a particle suspension, such as by ultrasound (e.g., if the particle suspension has been dried), can play an important role with regard to particle size distribution. The AUC method was used for determining the particle size distribution in the working examples described below. The values obtained are defined as integral mass distributions in 10% steps ($d_0$, $d_{10}$, $d_{20}$, . . . $d_{100}$). Thus, for example, the value $d_{50}$=0.9 µm means that 50% by weight of the particles have a diameter of up to 0.9 µm. Due to their small quantities, nanoparticulate impurities in magnetic particle samples generally cannot be determined quantitatively by any of the above methods.

Zeta Potential

The zeta potential refers to the potential difference between the medium and the stationary layer of fluid attached to the dispersed particles in the medium. Zeta potential can be determined from the electrophoretic mobility of finely dispersed loaded particle systems, as is well known in the art. The determination of the zeta potential is highly dependent on pH. In the case of silica-modified (i.e., silica-coated) particles, the pH-dependent charge is based on the following equilibrium reaction: $SiOH \leftrightarrow SiO^- + H^+$. In the working examples presented below, the zeta potential was determined in an alternating electrical field using the Zeta Sizer 2000 device from Malvern. The pH value at which the electrophoretic mobility approaches 0 is designated the isoelectric point; that is, the zeta potential is 0 mV at the isoelectric point. Alternatively the electrophoretic mobility can be determined by capillary electrophoresis in a direct current field. Additional literature can be found, for example, in brochures from Malvern, in "Bioanalytik" (Bioanalytics) by F. Lottspeich, Spektrum akademischer Verlag (Spectrum academic publishers) 1998 or in "Methoden der Biophysikalischen Chemie" (Methods of biophysical chemistry), R. Winter, "Teubner Studienbucher" Publishers, 1998.

High negative zeta potentials of, for example, −50 mV at alkaline pH values correlate with a high SiOH load on the particle surface.

Electron Spectroscopy for Chemical Analysis (ESCA)

The thickness of the silica coating of the magnetic particles can be determined by ESCA. Photoelectron spectroscopy carried out in a high vacuum has an information depth of about 5-10 nm. The area examined is about 5 mM2 and the detection limit is 0.1 atomic % for all detected elements. If the coating of a substrate is thinner than the exit depth of the photoelectrons of the substrate, lines appear in the ESCA spectrum from the elements of both regions. Assuming that the substrate is uniformly coated, the average thickness of the coating can be calculated from the intensity ratios of the two lines.

Inductively Coupled Plasma-Optical Emission Spectroscopy (ICP-OES)

ICP-OES is a technique for determining trace elements in a sample and is usually independent of the type of binding. The samples to be analyzed are decomposed into their elements using mineral acids in a total digestion process. In the examples described below, ICP-OES determination was carried out according to DIN-ISO 17025. In this method an inductively coupled argon plasma (ICP) is used as the excitation source and an optical system is used as the detector. The liquid samples are atomized in an atomization device (pneumatically or ultrasonically). The resulting aerosol is transported into the plasma, where it is dried, atomized, ionized, and electronically excited. The emitted light is detected by means of an optical system. Depending on the optical system used, it is possible to conduct simultaneous quantitative detection of more than 60 elements. In addition it is possible to obtain semi-quantitative overview spectra of unknown samples.

Specific Surface Area

The specific surface area of the particles can be determined, for example, by the BET (Brunauer, Emmet and Teller) test. In the examples below, determination of the specific surface area was performed by gas sorption according to DIN 66 131.

EXAMPLES

Example 1

Coating of Bayoxide E 7806 with Silica to a Target pH of 9.7

714.3 g of sodium silicate 37/40 (35% by weight in water) were added with stirring to 3285.7 g of water, a dilute 6.25% strength sodium silicate solution being obtained after stirring for 5 minutes. Then 1000.0 g of Bayoxide E 8706® magnetic particles were added with stirring in portions to the above solution, after which the mixture was stirred for a further hour at room temperature. An anchor-shaped stirrer was used at a speed of 250 rpm.

The stirrer was switched off, whereupon the black magnetic particle suspension slowly sedimented. After leaving it to stand for about 30 mins the supernatant became clearer, and after 60 mins about 3.8 L of the slightly cloudy, slightly colored supernatant were siphoned off with the aid of a glass tube leaving a volume of magnetic particles plus residual supernatant of about 0.5 L. 4 L of fresh water were added to the residue and the mixture was stirred for 10 mins. The stirring apparatus and speed were the same as indicated above. After this first separation step ("working cycle") the pH value of the nanoparticle suspension was 11.2.

The separation steps (stirring, sedimentation, and resuspension) were repeated until a target pH value of about 9.7 was obtained. With each additional working cycle of stirring, sedimentation, and resuspension, the supernatant became clearer and the pH value of the resuspended particles was reduced. The following is a list of the pH values of the individual steps:

2nd separation step: pH: 10.8
3rd separation step: pH: 10.4
4th separation step: pH: 10.1
5th separation step: pH: 10.0
6th separation step: pH: 9.8
7th separation step: pH: 9.7

The target pH value was reached after the 7th separation step. After the $7^{th}$ step, about 3.8 L of the colorless, transparent supernatant were siphoned off, as described above. The supernatant was free of colored and nanoparticulate contaminants. The remaining slurry—about 1200 g of a black nanoparticle suspension—was adjusted to a final concentration of 50 mg/ml by dilution with water, after which the pH value was stabilized at 9.7 by adding CHES (2-cyclohexylaminoethane-sulphonic acid) buffer to a concentration of 0.1N.

Example 2

Physical Characterization of Silica-Coated Bayoxide E 7806 Particles

The end product from Example 1, which is also hereinafter referred to as HIE 13 759 R3, was characterized as follows by determining the pH value, the zeta potential, and the Fe and Si contents according to ICP OES and ESCA. The values for the HIE 13 759 R3 material were compared with the untreated Bayoxide particles. The results are indicated in Table 1.

TABLE 1

| | pH | Zeta potential (mV) at a pH | ICP OES Fe/Si ratio after total hydrolysis in % by weight | ESCA Surface analysis in atomic % | | |
|---|---|---|---|---|---|---|
| | | | | Fe | Si | Fe/Si |
| Bayoxide E 8706 | 7.5 | −24.8 | 159.2 Fe/Si | 21.3 | 2.0 | 10.6 |
| Bayoxide E 8706 with a silica layer (HIE 13 759 R3) | 9.7 | −51.8 | 46.7 | 13.2 | 6.4 | 2.1 |

The zeta potential as determined for HIE 13 759 R3 at several pH values was as follows: at pH 10, −55.7 mV; at pH 4, −42 mV; and at pH 2.76, 0 mV (the isoelectric point). At even lower pH values the zeta potential was positive.

For Bayoxide E 8706 an Fe content of 78% by weight and an Si content of 0.49% by weight was determined by ICP OES, thus producing a Fe/Si ratio of 159.2. Compared with Bayoxide E 8706, the Fe/Si ratio of the silica-modified end product revealed higher quantities of Si. Compared with the starting product, the Fe/Si ratio of the silica-modified end product determined by ESCA also reveals higher quantities of Si. A layer thickness of 0.88 nm was calculated from the Si content of 6.6% by weight of silica.

Although the pH of 7.5 of the starting product reveals that it does not have an acidic surface, with the aid of the multi-step fractionation process according to the invention, a stable silica modification of the Bayoxide E 8706 surface was obtained, as is shown by the results.

Particle sizes and particle size distribution were determined by AUC after ultrasonic treatment (1 min sonication using a wand sonicator) of a particle suspension diluted to 0.12 g/L. The results are shown in Table 2.

TABLE 2

| | Bayoxide E 8706 (size in μm) | Bayoxide E 8706//silica (size in μm) |
|---|---|---|
| $d_0$ | 0.1439 | 0.2235 |
| $d_{10}$ | 0.7234 | 0.6239 |
| $d_{20}$ | 0.8940 | 0.7414 |
| $d_{30}$ | 1.0316 | 0.8330 |
| $d_{40}$ | 1.1598 | 0.9159 |
| $d_{50}$ | 1.2861 | 0.9951 |
| $d_{60}$ | 1.4127 | 1.0746 |
| $d_{70}$ | 1.5380 | 1.1574 |
| $d_{80}$ | 1.6762 | 1.2525 |
| $d_{90}$ | 1.8809 | 1.3859 |
| $d_{100}$ | 3.2827 | 1.8636 |

The above results show that the silica treatment did not produce any significant changes in the particle size distribution. There was a slight tendency for the particle size distribution to be narrowed after the silica treatment, due to the many washing and separation steps.

The magnetic properties of the original and silica-coated particles are shown in Table 3. As the results show, the magnetic properties were not changed to any significant degree as a result of the silica coating.

TABLE 3

| | Bs (emu/g) | Br (emu/g) | IHC (Oe) |
|---|---|---|---|
| Bayoxide E 8706 | 90.0 | 5.4 | 57.4 |
| Bayoxide E 8706/ Silica (HIE 13 759 R3) | 86.1 | 7.7 | 72.9 |

Particle morphology of the untreated and silica-coated particles was determined by REM. No differences were detected between the Bayoxide E 8706 and Bayoxide E 8706/silica samples.

The HIE 13 759 R3 particles were tested for nucleic acid binding ability and showed very consistent recovery from $10^6$ down to 50 copies/mL. The nucleic acid target was a sequence obtained from Hepatitis C virus (HCV, genotype 1a). The target sequence was ACCATGAATCACTCCCCTGTGAGGAACTACTGTCTTCACGCAGAAAGCGTCTAGCCAT GGCGTTAG TATGAGTGTCGTACAGCCTCCAGGACCCCCCCTCCCGGGAGAGCCATAGTGGTCTGCGG (SEQ ID NO:1). The HIE 13 759 R3 particles were added to a solution containing the target DNA at varying copy number. The particles were allowed to bind the target, after which the particles were separated using a magnetic field. The bound nucleic acids were then eluted, and the target sequence was detected in the eluted nucleic acids by quantitative PCR. At the 50 copy/mL titer, the target was detected 60% of the time.

Example 3

Coating of Bayoxide E 7806 with Silica to a Target pH of 7.8

The reaction, sedimentation, and resuspension process of Example 1 was carried out, except that the separation steps were not terminated after seven cycles (pH of 9.7), but instead five additional separation steps (working cycles) were carried out until a pH value of 7.8 was obtained. The physical characterization revealed a zeta potential of −43 mV at pH 7.8, indicating a reduced silica load. The recovery of HCV RNA from these particles when compared to HIE 13 759 was much less consistent, and the detection at 50 copies/mL dropped to ~30%.

What is claimed is:

1. A composition comprising silica-coated magnetic particles produced by a process comprising the steps of:

(a) reacting magnetic particles with a waterglass solution;

(b) sedimenting the particles;

(c) removing a supernatant after sedimentation of the magnetic particles;

(d) resuspending the sedimented particles to form an aqueous suspension; and (e) repeating steps (b) through (d) until the pH of the aqueous suspension is in the range from about pH 9.4 to about pH 10.0 wherein said silica-coated magnetic particles are in the aqueous suspension.

2. The composition of claim 1, wherein 5 to 15 cycles of sedimenting and resuspending the particles are performed.

3. The composition of claim 1, wherein the final particle suspension comprises a buffer.

4. The composition of claim 3, wherein the buffer is 2-cyclohexylaminoethane-sulphonic acid.

5. The composition of claim 3, wherein the pH of the final particle suspension is about 9.5 to about 9.9.

6. The composition of claim 5, wherein the pH of the final particle suspension is about 9.7.

7. The composition of claim 1, wherein the pH of the suspension of magnetic particles in waterglass solution formed in step (a) has an initial pH of about 10 to about 13.

8. The composition of claim 1, wherein the zeta potential at pH 7 of the particles is more negative than −40 mv.

9. The composition of claim 8, wherein the zeta potential at pH 7 is in the range of about −48 to about −58 mV.

10. The composition of claim 1, wherein the isoelectric point of the particles is in the range of pH 2.7 to pH 2.8.

11. The composition of claim 1, wherein the magnetic particles comprise Fe304.

12. The composition of claim 11, wherein the magnetic particles consist of granular Fe304 having a particle size distribution characterized by a d50 value in the range of about 0.5 to about 1.5 μm.

13. The composition of claim 12, wherein the magnetic particles consist of granular Fe304 having a particle size distribution characterized by a d50 value of about 1 μm.

14. The composition of claim 1, wherein at least 50% of the silica-coated particles have a diameter of less than 2 μm.

15. The composition of claim 14, wherein at least 90% of the silica-coated particles have a diameter of less than 2 μm.

16. The composition of claim 1, wherein the silica coating of the particles is less than about 1 nm in thickness.

17. The composition of claim 1, wherein the Si content of the silica-coated particles is in the range of about 6 to about 7 atomic percent.

18. The composition of claim 1, wherein the Fe/Si atomic ratio of the silica-coated particles is in the range of about 2 to about 2.5.

19. The composition of claim 1, wherein the silica-coated particles bind nucleic acid in a chaotrope solution.

20. The composition of claim 1, wherein the silica-coated particles have a saturation magnetism of about 80 to about 90 emu/g, a remanence flux density of about 5 to about 7 emu/g, and a coercivity value of about 50 to about 80 Oe.

21. The composition of claim 1, wherein the silica-coated particles are capable of recovering a PCR-detectable nucleic acid sequence present in a sample at a concentration from about 50 to about one million copies per ml.

22. A process of preparing silica-coated magnetic particles, the process comprising the steps of:
   (a) reacting magnetic particles with a waterglass solution;
   (b) sedimenting the particles;
   (c) removing a supernatant after sedimentation of the magnetic particles;
   (d) resuspending the sedimented particles to form an aqueous suspension; and
   (e) repeating steps (b) through (d) until the pH of the aqueous suspension is in the range from about pH 9.4 to about pH 10.0.

23. The process of claim 22, wherein the final pH of the aqueous suspension is about 9.7.

24. The process of claim 22, wherein step of reacting is carried out for about 30 minutes at about 15 to 40° C.

25. The process of claim 22, wherein the step of sedimenting is performed by allowing the particles to settle without stirring at about 1×g.

26. The process of claim 25, wherein the step of sedimenting is performed by allowing the particles to settle for about 1 hour.

27. The process of claim 22, wherein the step of sedimenting comprises the use of magnetism or centrifugation.

28. The process of claim 22, wherein the step of resuspending comprises stirring for at least 30 minutes.

29. The process of claim 22, further comprising the step of:
   (e) suspending the silica-coated particles in a buffer at a pH in the range of about pH 9.5 to about pH 9.8.

30. The process of claim 22, wherein the silica-coated particles are subsequently analyzed for at least one characteristic selected from particle size distribution, Fe content, Si content, zeta potential, saturation magnetism, remanence flux density, and coercivity.

31. The process of claim 22, wherein the zeta potential at pH 7 of the particles is more negative than −40 mv.

32. The process of claim 31, wherein the zeta potential at pH 7 is in the range of about −48 to about −58 mV.

33. A method of analyzing a nucleic acid in a sample, comprising binding said nucleic acid to a suspension of silica-coated magnetic beads produced according to the process of claim 22.

34. A kit comprising a composition according to claim 1 and instructions for the use thereof in a method of isolating or analyzing a nucleic acid.

* * * * *